(12) United States Patent
Beppu et al.

(10) Patent No.: US 10,710,821 B2
(45) Date of Patent: Jul. 14, 2020

(54) CONVEYANCE SYSTEM

(71) Applicant: Azbil Corporation, Chiyoda-ku (JP)

(72) Inventors: Hisashi Beppu, Chiyoda-ku (JP); Yoichi Okawa, Chiyoda-ku (JP); Mitsuharu Tanaka, Chiyoda-ku (JP)

(73) Assignee: Azbil Corporation, Chiyoda-ku (JP)

( * ) Notice: Subject to any disclaimer, the term of this patent is extended or adjusted under 35 U.S.C. 154(b) by 0 days.

(21) Appl. No.: 16/336,672

(22) PCT Filed: Sep. 26, 2016

(86) PCT No.: PCT/JP2016/078244
§ 371 (c)(1),
(2) Date: Mar. 26, 2019

(87) PCT Pub. No.: WO2018/055758
PCT Pub. Date: Mar. 29, 2018

(65) Prior Publication Data
US 2020/0062516 A1 Feb. 27, 2020

(51) Int. Cl.
*B65G 54/02* (2006.01)
*F26B 25/00* (2006.01)
*A61L 2/04* (2006.01)
*F26B 5/06* (2006.01)

(52) U.S. Cl.
CPC ............ *B65G 54/02* (2013.01); *A61L 2/04* (2013.01); *F26B 5/06* (2013.01); *F26B 25/001* (2013.01); *B65G 2207/26* (2013.01)

(58) Field of Classification Search
CPC ..... A61L 2/04; A61L 2/06; A61L 2/07; A61L 2/10; A61L 2/206; B65G 54/02; B65G 54/025; B65G 2207/26; F26B 5/06; F26B 5/001
See application file for complete search history.

(56) References Cited

U.S. PATENT DOCUMENTS

| | | | |
|---|---|---|---|
| 2008/0134537 A1 | 6/2008 | Damen | |
| 2013/0185952 A1 | 7/2013 | Christ | |
| 2015/0246777 A1 | 9/2015 | Trebbi et al. | |

FOREIGN PATENT DOCUMENTS

| | | |
|---|---|---|
| CN | 100582624 C | 1/2010 |
| CN | 104285114 A | 1/2015 |
| JP | 2008-501598 A | 1/2008 |
| JP | 2015-521269 A | 7/2015 |

(Continued)

OTHER PUBLICATIONS

International Search Report dated Nov. 8, 2016 in PCT/JP2016/078244 filed Sep. 26, 2016.

(Continued)

*Primary Examiner* — Lessanework Seifu
(74) *Attorney, Agent, or Firm* — Oblon, McClelland, Maier & Neustadt, L.L.P.

(57) ABSTRACT

A conveyance system includes a chamber 1, a plate 7A disposed in the chamber 1, the plate 7A being used for disposing an article thereon, an in-chamber bridge 19 disposed in the chamber 1 and capable of coming into contact with the plate 7A, a moving member 3A that moves along the in-chamber bridge 19 and the plate 7A to move the article on the in-chamber bridge 19 and the plate 7A, and a sterilization device 100 that sterilizes an interior of the chamber 1, in which the chamber 1 is allowed to be tightly sealed, with the moving member 3A disposed on the in-chamber bridge 19.

10 Claims, 25 Drawing Sheets

(56) References Cited

FOREIGN PATENT DOCUMENTS

| | | |
|---|---|---|
| WO | WO 2005/012671 A1 | 2/2005 |
| WO | WO 2005/121672 A1 | 12/2005 |
| WO | WO 2013/136157 A1 | 9/2013 |
| WO | WO 2016/067872 A1 | 5/2016 |

OTHER PUBLICATIONS

Combined Chinese Office Action and Search Report dated Mar. 27, 2020 in Chinese Patent Application No. 201680089599.8 (with English translation and English translation of Category of Cited Documents), citing documents AO and AP therein, 16 pages.

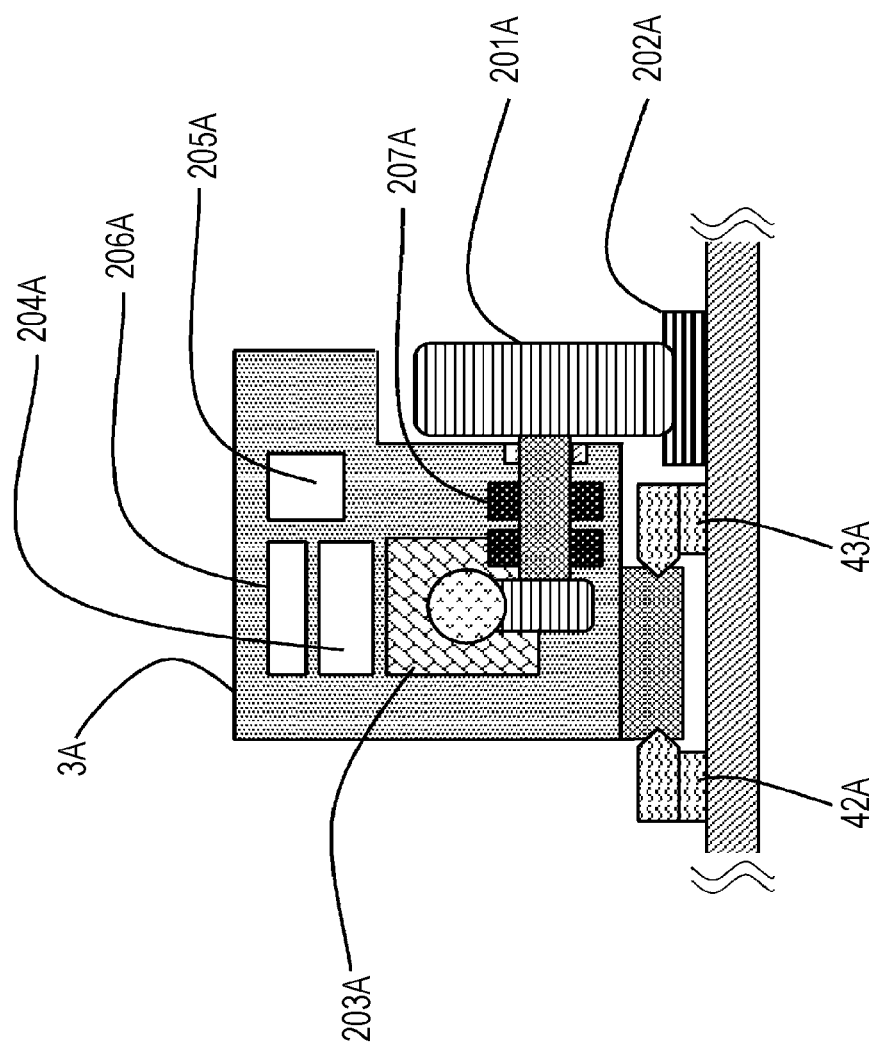

CONVEYANCE SYSTEM

TECHNICAL FIELD

The present invention relates to a conveyance technique, and in particular, to a conveyance system.

BACKGROUND ART

In a process of manufacturing articles such as pharmaceuticals and foods, a chamber such as a freeze-drying chamber may be used (for example, PTLs 1 to 4). The articles are moved by a moving member and conveyed inside and outside the chamber. The chamber may be sterilized to prevent microorganisms such as bacteria from entering the articles. For example, in a freeze-drying chamber, the components in the chamber, a plate on which the articles are disposed, and a pipe for supplying a refrigerant are sterilized with high-pressure steam.

CITATION LIST

Patent Literature

PTL 1: International Publication No. 2005/121672
PTL 2: International Publication No. 2005/121671
PTL 3: International Publication No. 2013/136157
PTL 4: U.S. Patent Application Publication No. 2013/0185952

SUMMARY OF INVENTION

Technical Problem

The inventors have found that stabilizing also the moving member for moving articles inside and outside the chamber further suppresses contamination of microorganisms into the articles. Accordingly, an object of the present invention is to provide a conveyance system capable of sterilizing the moving member for moving articles inside and outside the chamber.

Solution to Problem

According to an aspect of the present invention, a conveyance system is provided which includes a chamber, a plate disposed in the chamber, the plate being used for disposing an article thereon, an in-chamber bridge disposed next to the plate in the chamber, a moving member that moves along the in-chamber bridge and the plate to move the article on the in-chamber bridge and the plate, and a sterilization device that sterilizes an interior of the chamber. The chamber is allowed to be tightly sealed, with the moving member disposed on the in-chamber bridge.

In the conveyance system, the sterilization device may pressurize or heat the interior of the chamber.

The conveyance system may further include an out-of-chamber bridge disposed outside a door of the chamber, the out-of-chamber bridge being contactable with the in-chamber bridge. The moving member may move along the out-of-chamber bridge, the in-chamber bridge, and the plate.

In the conveyance system, the in-chamber bridge may be movable between the out-of-chamber bridge and the plate, the out-of-chamber bridge may be movable toward the in-chamber bridge, or the out-of-chamber bridge may be rotatable.

The conveyance system may further include a first rod-like member disposed at the out-of-chamber bridge and including a magnetic body, a second rod-like member disposed at the in-chamber bridge and including a magnetic body, a third rod-like member disposed along the plate in the chamber and including a magnetic body, and a drive unit that rotates the first rod-like member.

In the conveyance system, when the out-of-chamber bridge, the in-chamber bridge, and the plate come into contact with each other, the first, second, and third rod-like members may be connected to each other.

In the conveyance system, the moving member may include a magnetic body and may be configured to face part of peripheries of the first to third rod-like members.

In the conveyance system, the moving member may move along the first, second, and third rod-like members as the first, second, and third rod-like members rotate.

In the conveyance system, the chamber may include a first chamber containing the plate and including a first door between the in-chamber bridge and the plate, and a second chamber containing the in-chamber bridge and including a second door between the out-of-chamber bridge and the in-chamber bridge, and the first and second doors may be allowed to being closed, with the moving member disposed on the in-chamber bridge.

The conveyance system may further include a contact member connected to the moving member and being in contact with the article.

In the conveyance system, the chamber may be a freeze-drying chamber, and the article may contain a pharmaceutical.

Advantageous Effects of Invention

According to the present invention, a conveyance system capable of sterilizing a moving member for moving articles inside and outside a chamber can be provided.

BRIEF DESCRIPTION OF DRAWINGS

FIG. 25 is a schematic sectional view of a moving member according to the yet further embodiment.

DESCRIPTION OF EMBODIMENTS

Embodiments of the present invention will be described hereinbelow. In the following description of the drawings, the same or similar parts are represented by the same or similar signs. However, the drawings are schematic. Accordingly, specific dimensions and so on should be determined with reference to the following description. For the relationship between the drawings, it is needless to say that the dimensional relationship and ratios may differ.

First Embodiment

Figure 1:
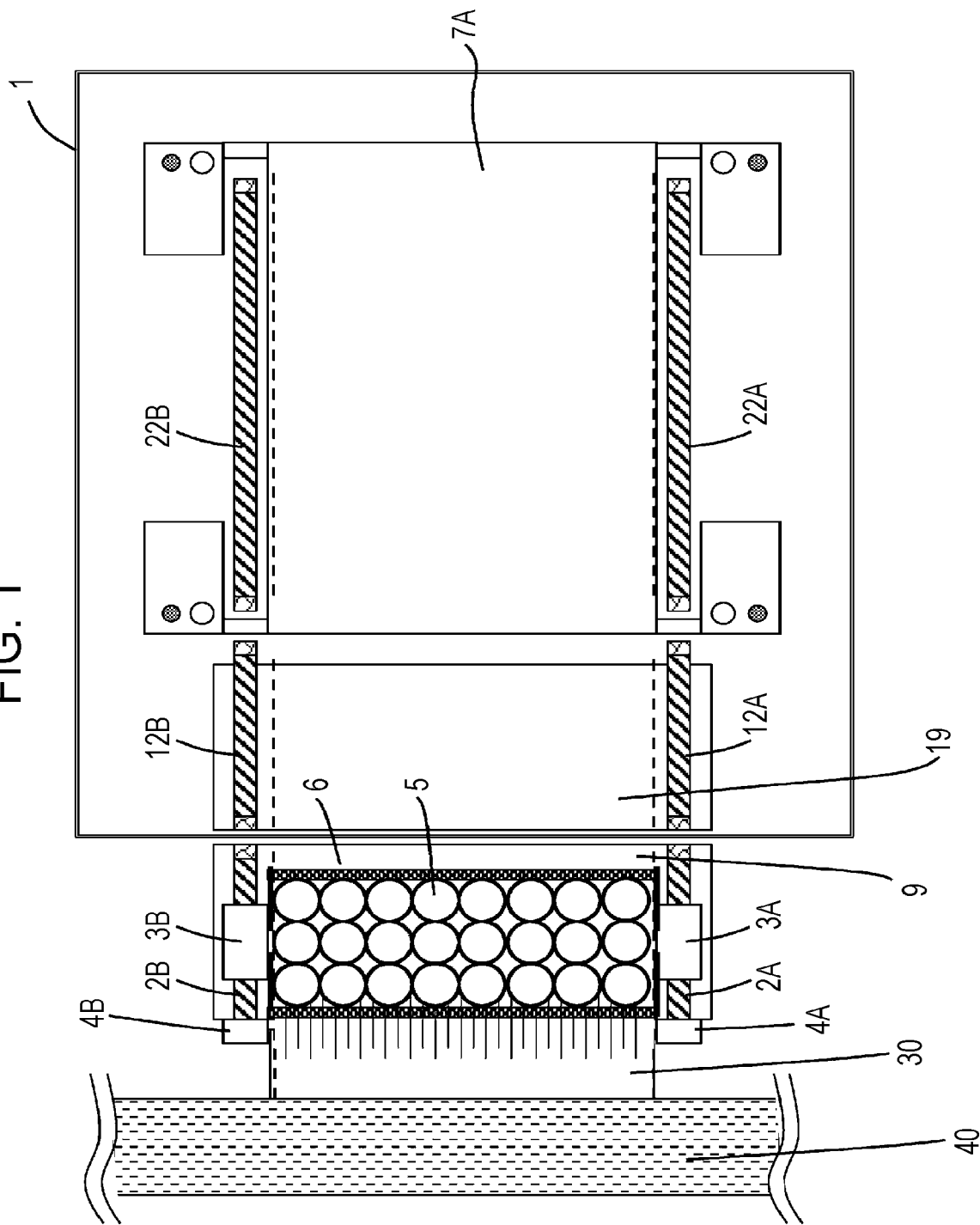
FIG. 1 is a schematic top view of a conveyance system according to a first embodiment.
Figure 2:
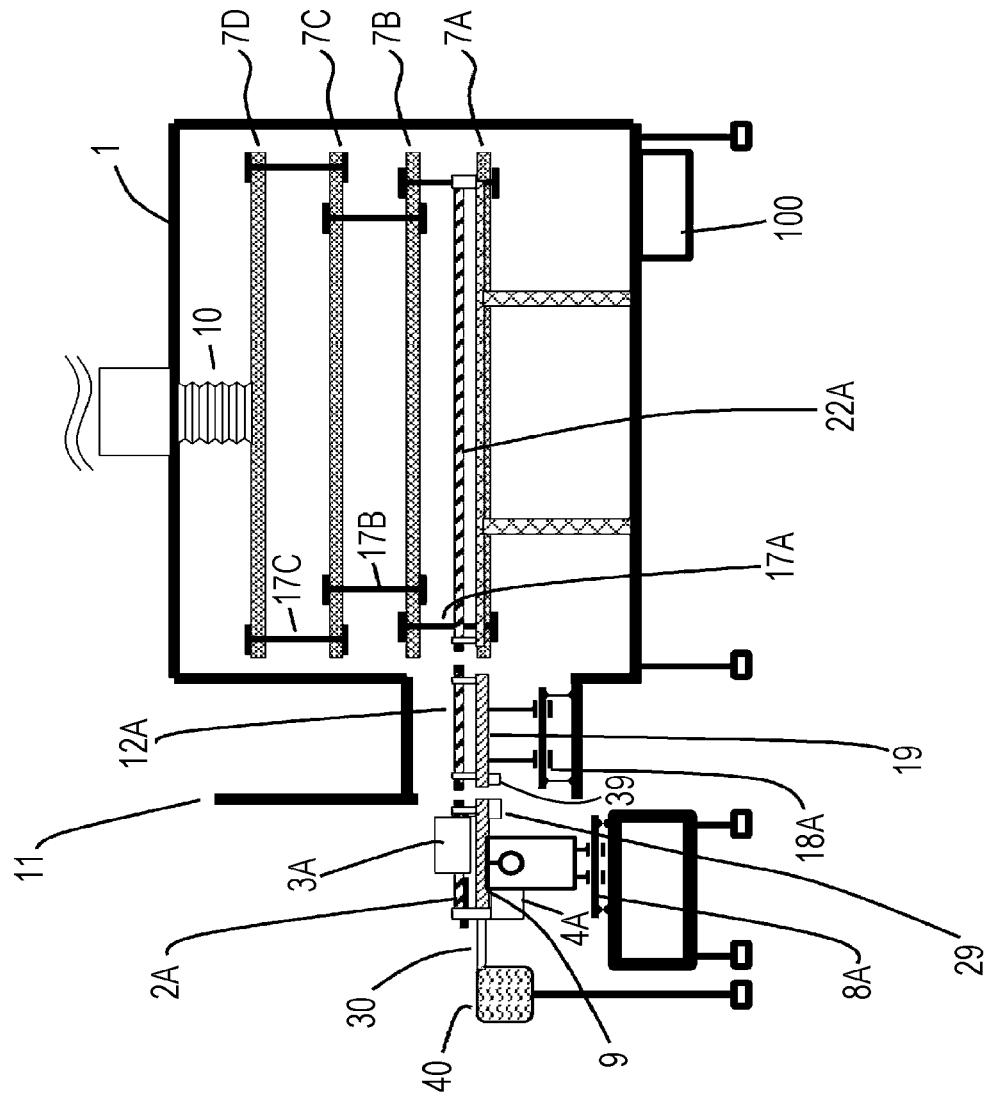
FIG. 2 is a schematic side view of the conveyance system according to the first embodiment.

As illustrated in FIGS. 1 and 2, a conveyance system according to a first embodiment includes a chamber 1, a plate 7A disposed in the chamber 1 and used in disposing articles 5 thereon, an in-chamber bridge 19 disposed next to the plate 7A in the chamber 1, an out-of-chamber bridge 9 that is disposed outside a door 11 of the chamber 1 and that is capable of contact with the in-chamber bridge 19, moving members 3A and 3B that move along the out-of-chamber bridge 9, the in-chamber bridge 19, and the plate 7A to move the articles 5 on the out-of-chamber bridge 9, the in-chamber bridge 19, and the plate 7A, and a sterilization device 100, illustrated in FIG. 2, for sterilizing the interior of the chamber 1. In the conveyance system according to the first embodiment, the chamber 1 can be tightly sealed, with the moving member 3A disposed on the in-chamber bridge 19.

As illustrated in FIG. 1, the chamber 1 is, for example, a temperature regulated chamber having a space in which the articles 5 are disposed and whose temperature is regulated. The temperature regulation chamber may be, for example, a freeze-drying chamber. An example of the articles 5 is a phial containing medicine. In the case where the chamber 1 is a freeze-drying chamber, the articles 5 are disposed on the plate 7A in the chamber 1, and the medicine or the like in the articles 5 is freeze-dried.

As illustrated in FIG. 2, plates 7B, 7C, and 7D are disposed above the plate 7A in the chamber 1. The plate 7D is hung from the ceiling of the chamber 1 with a cylinder covered with a bellows cover 10. The plate 7C is hung from the plate 7D with a hook 17C. The plate 7B is hung from the plate 7C with a hook 17B. The plate 7A is hung from the plate 7B with a hook 17A.

Figure 3:
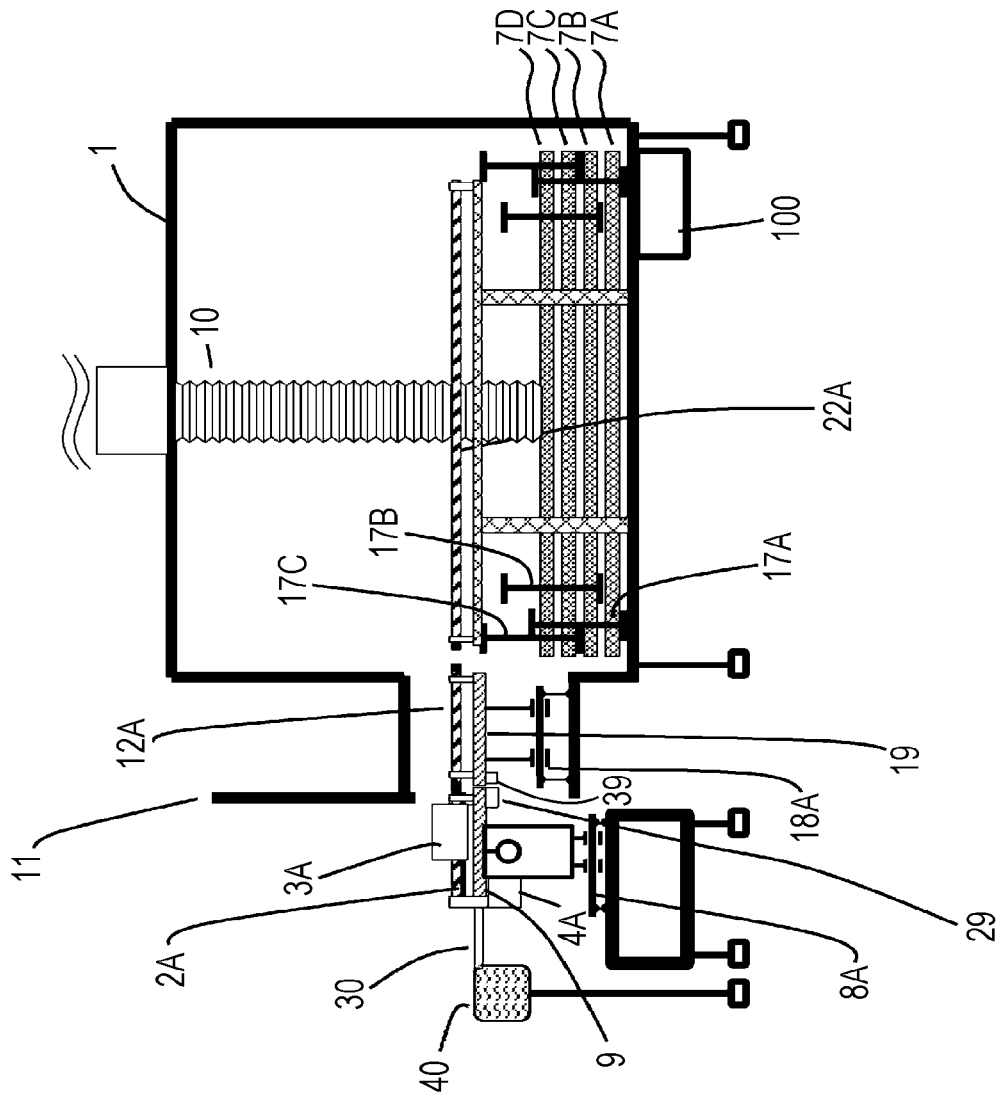
FIG. 3 is a schematic side view of the conveyance system according to the first embodiment.
Figure 4:
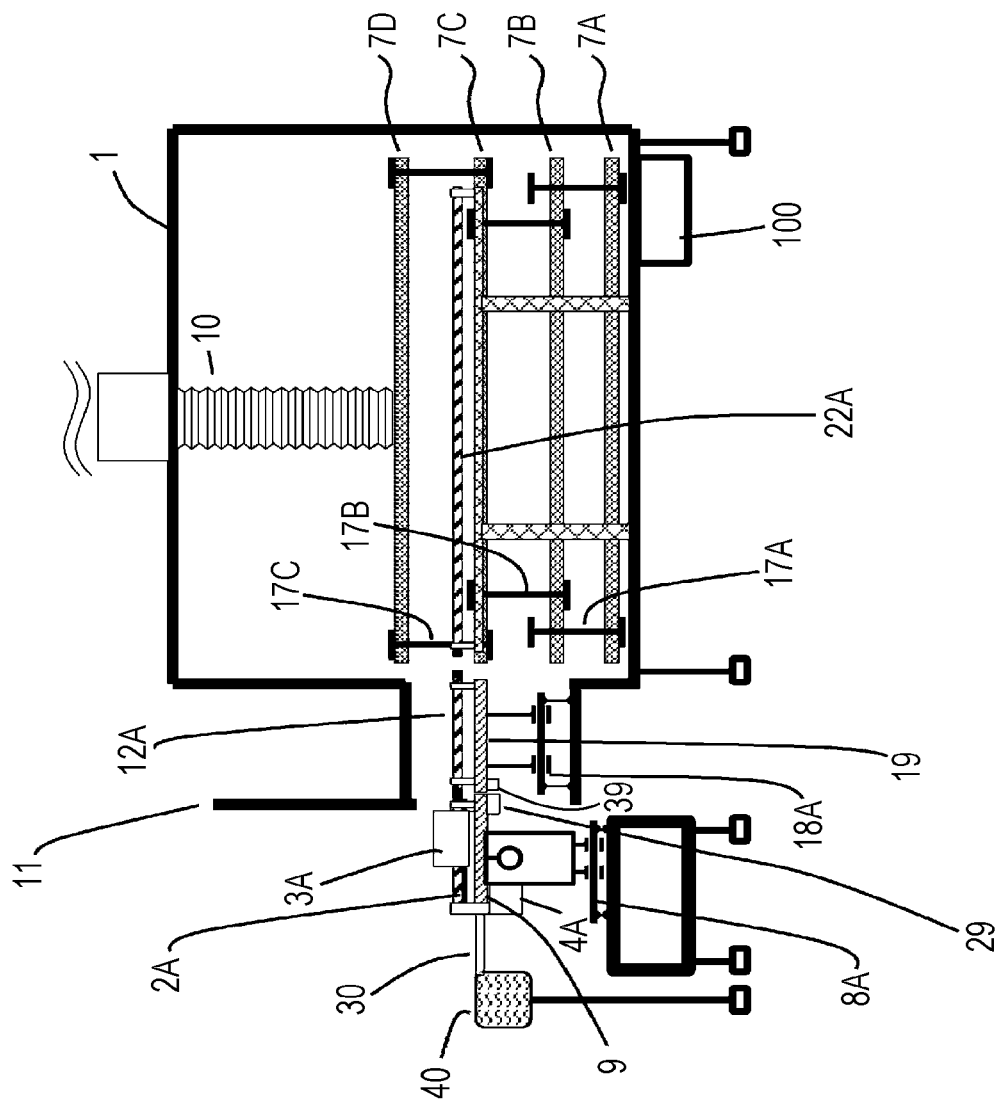
FIG. 4 is a schematic side view of the conveyance system according to the first embodiment.

As illustrated in FIG. 3, if the chamber 1 is not to be used, the cylinder covered with the bellows cover 10 may extend so that the plates 7A, 7B, 7C, an 7D are disposed in the lower part of the chamber 1. When the articles 5 are disposed on the plate 7C, the cylinder covered with the bellows cover 10 hangs the plates 7A, 7B, 7C, and 7D so that the surface of the plate 7C and the surface of the in-chamber bridge 19 are flush with each other, as illustrated in FIG. 4.

Figure 5:
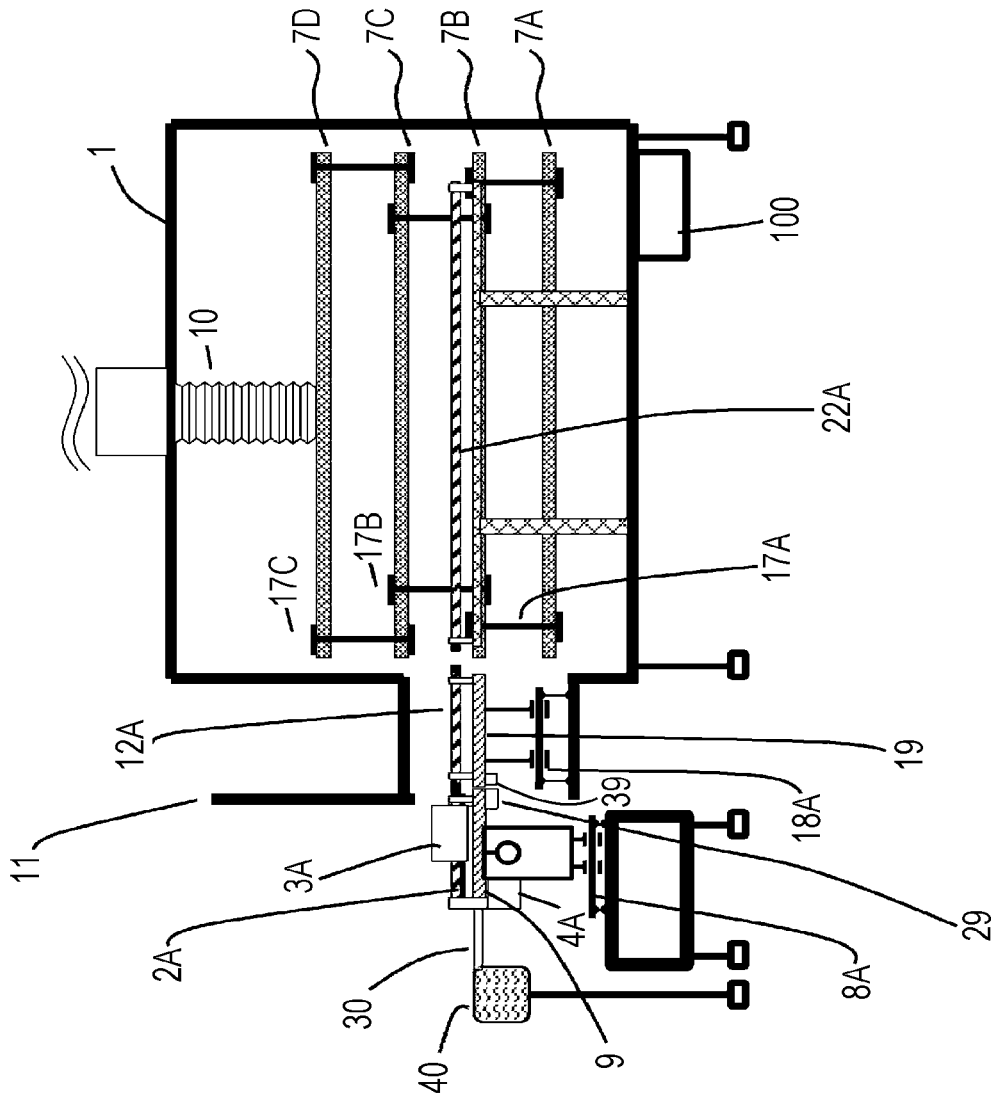
FIG. 5 is a schematic side view of the conveyance system according to the first embodiment.
Figure 6:
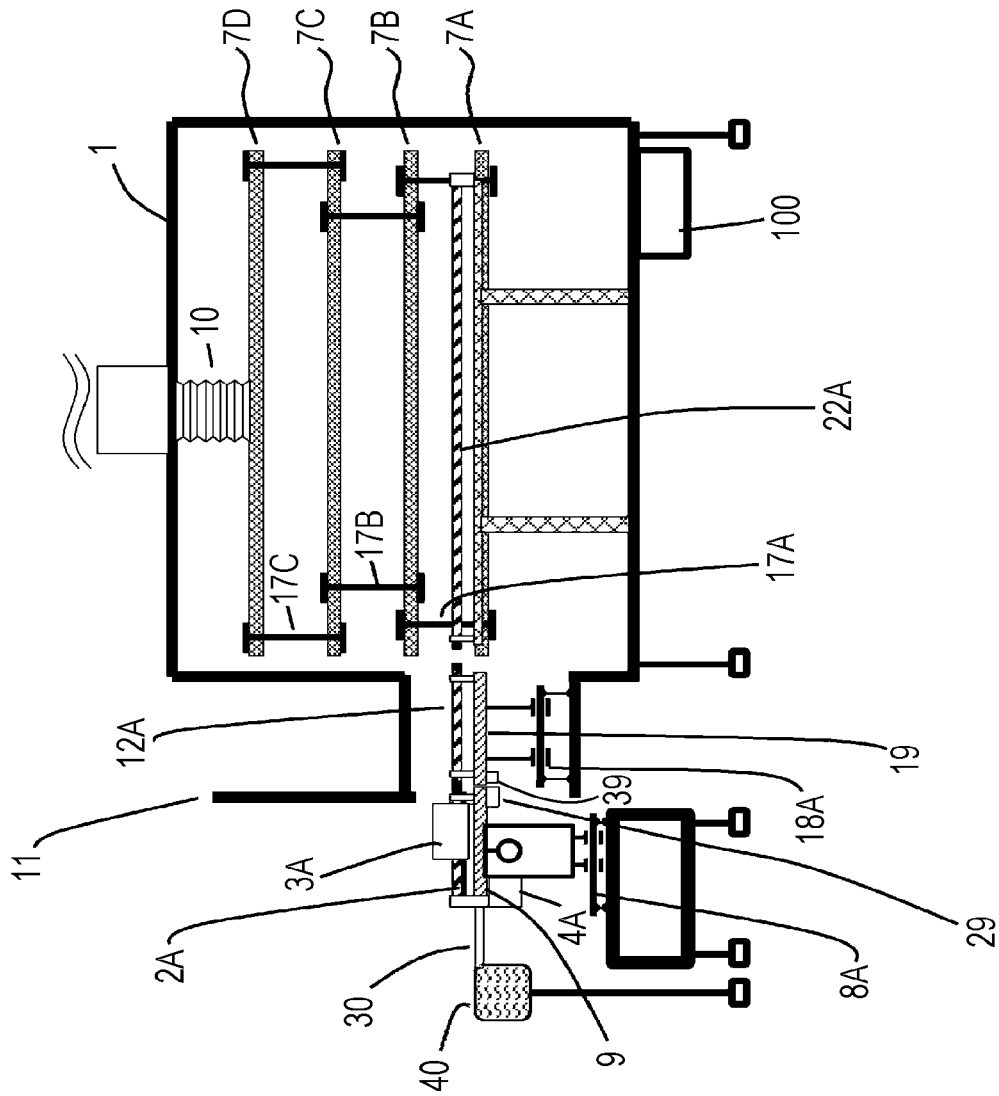
FIG. 6 is a schematic side view of the conveyance system according to the first embodiment.

When the articles 5 are disposed on the plate 7B, the cylinder covered with the bellows cover 10 hangs the plates 7A, 7B, 7C, and 7D so that the surface of the plate 7B and the surface of the in-chamber bridge 19 are flush with each other, as illustrated in FIG. 5. When the articles 5 are disposed on the plate 7A, the cylinder covered with the bellows cover 10 hangs the plates 7A, 7B, 7C, and 7D so that the surface of the plate 7A and the surface of the in-chamber bridge 19 are flush with each other, as illustrated in FIG. 6.

The sterilization device 100 sterilizes the interior of the chamber 1 by pressurizing or heating the interior of the chamber 1. A method by which the sterilization device 100 sterilizes the interior of the chamber 1 is not particularly limited. The interior of the chamber 1 may be sterilized using, for example, a high-pressure steam sterilization method, a dry heat sterilization method, an ethylene oxide gas sterilization method, a radiation sterilization method, or an ultraviolet sterilization method.

Figure 7:
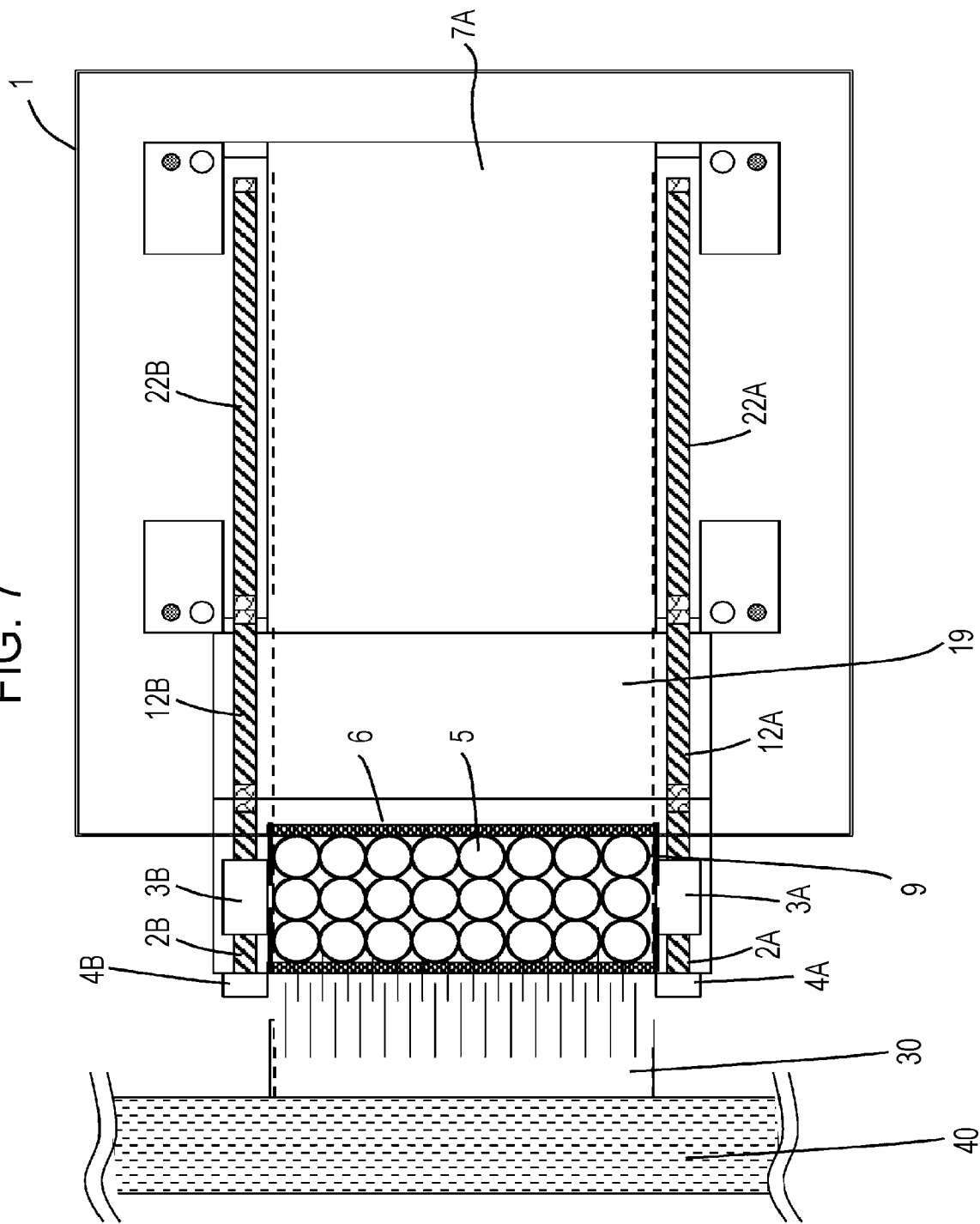
FIG. 7 is a schematic top view of the conveyance system according to the first embodiment.
Figure 8:
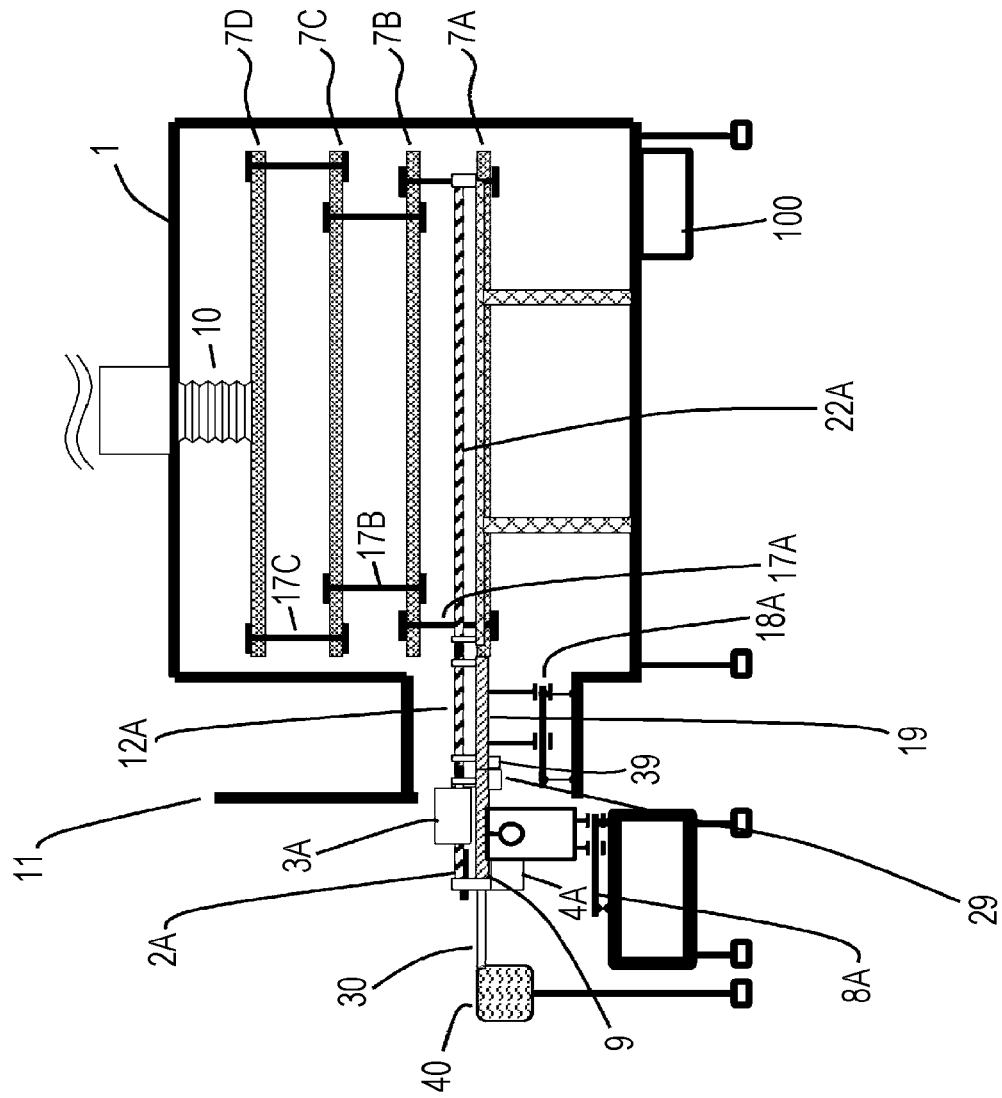
FIG. 8 is a schematic side view of the conveyance system according to the first embodiment.

The in-chamber bridge 19 is guided by a guide rail 18A so as to be able to translate between the out-of-chamber bridge 9 and the plate 7A in the chamber 1. The in-chamber bridge 19 is pushed by the out-of-chamber bridge 9 to come close the plate 7A into contact with the plate 7A, as illustrated in FIGS. 6, 7, and 8, for example. The term "contact" refers to contact so that the articles 5 can slide from the surface of the out-of-chamber bridge 9 to the surface of the plate 7A. There may be such a gap between the out-of-chamber bridge 9 and the plate 7A that the articles 5 do not fall. The in-chamber bridge 19 is separated from the plate 7A, for example, by being drawn by the out-of-chamber bridge 9.

The out-of-chamber bridge 9 is guided by the guide rail 8A so as to be able to translate in a direction toward the in-chamber bridge 19 and in a direction away from the in-chamber bridge 19 outside the chamber 1. The out-of-chamber bridge 9 includes, for example, a motor, so as to be self-propelled.

As illustrated in FIGS. 6 and 8, the out-of-chamber bridge 9 is provided with a coupler 29 at an end facing the in-chamber bridge 19. The in-chamber bridge 19 is provided with a coupler 39 at an end facing the out-of-chamber bridge 9. The coupler 29 and the coupler 39 can be connected together. The couplers 29 and 39 may include a magnet or an electric locking mechanism. For example, the out-of-chamber bridge 9 draws the in-chamber bridge 19 in a direction away from the plate 7A via the couplers 29 and 39. The couplers 29 and 39 may be configured to be separated from each other at a predetermined position.

Figure 9:
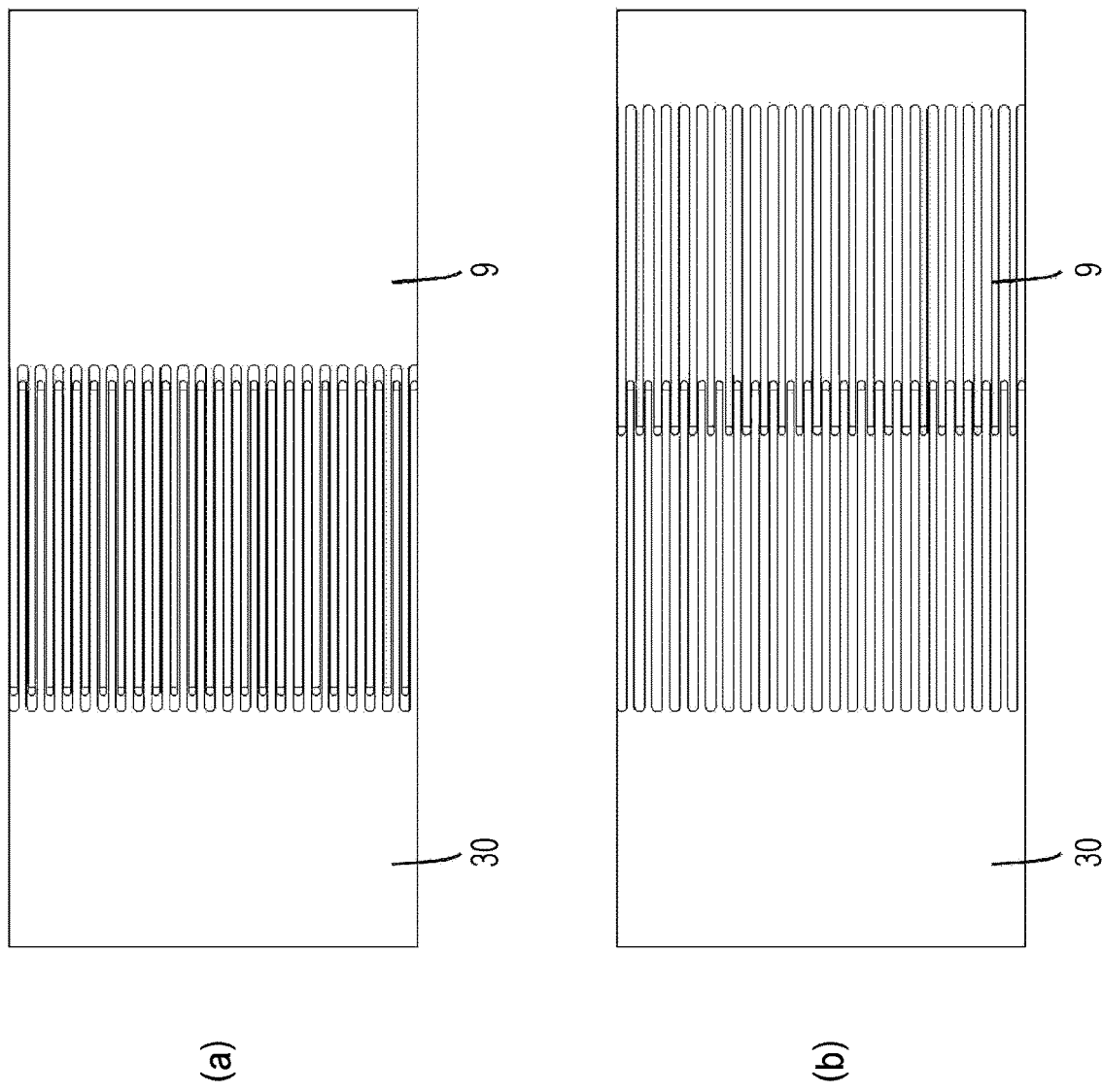
FIG. 9 is a schematic enlarged top view of the conveyance system according to the first embodiment.

A conveyer 40 is disposed on the side of the out-of-chamber bridge 9, opposite to the end facing the in-chamber bridge 19, with a fixing plate 30 disposed therebetween. The conveyer 40 conveys the articles 5 to be processed in the chamber 1. The conveyer 40 also conveys the articles 5 processed in the chamber 1. Since the out-of-chamber bridge 9 is movable as described above, an end of the fixing plate 30 and an end of the out-of-chamber bridge 9 may have a comb-like structure to be engaged with each other, as illustrated in FIG. 9(a). As illustrated in FIG. 9(b), even if the out-of-chamber bridge 9 moves in a direction away from the fixing plate 30, if the gap between the combs is smaller than the article 5, the article 5 does not fall through the gap.

As illustrated in FIG. 1, the out-of-chamber bridge 9 includes first rod-like members 2A and 2B each including a magnetic body parallel to each other. The out-of-chamber bridge 9 further includes a drive unit 4A that rotates the first rod-like member 2A around the central axis and a drive unit 4B that rotates the first rod-like member 2B around the central axis. The in-chamber bridge 19 includes second rod-like members 12A and 12B parallel to each other, each including a magnetic body. In the chamber 1, third rod-like members 22A and 22B each including a magnetic body are provided parallel to each other along the plate 7A.

Couplers are disposed at one end of the first rod-like member 2A, both ends of the second rod-like member 12A, and one end of the third rod-like member 22A. As illustrated in FIG. 6, when the out-of-chamber bridge 9 and the in-chamber bridge 19 come into contact with each other, the first and second rod-like members 2A and 12A are connected to each other by the couplers. As illustrated in FIG. 8, when the in-chamber bridge 19 and the plate 7A come into contact with each other, the second and third rod-like members 12A and 22A are connected to each other by the couplers.

Figure 10:
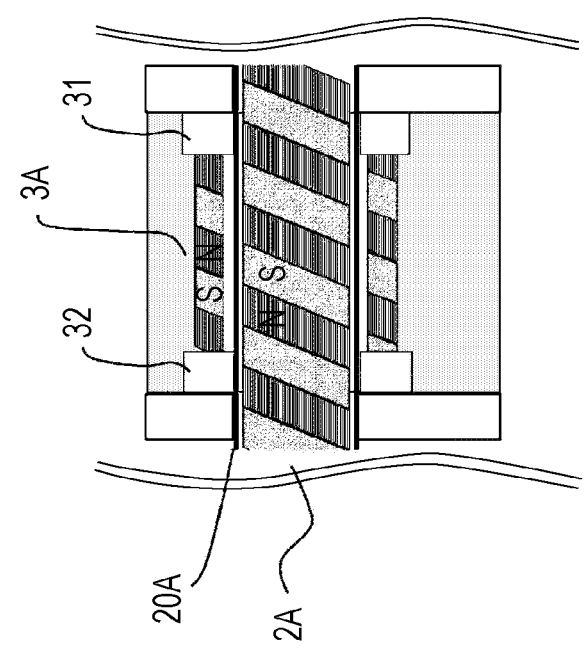
FIG. 10 is a sectional view of a rod-like member and a moving member according to the first embodiment.
Figure 11:
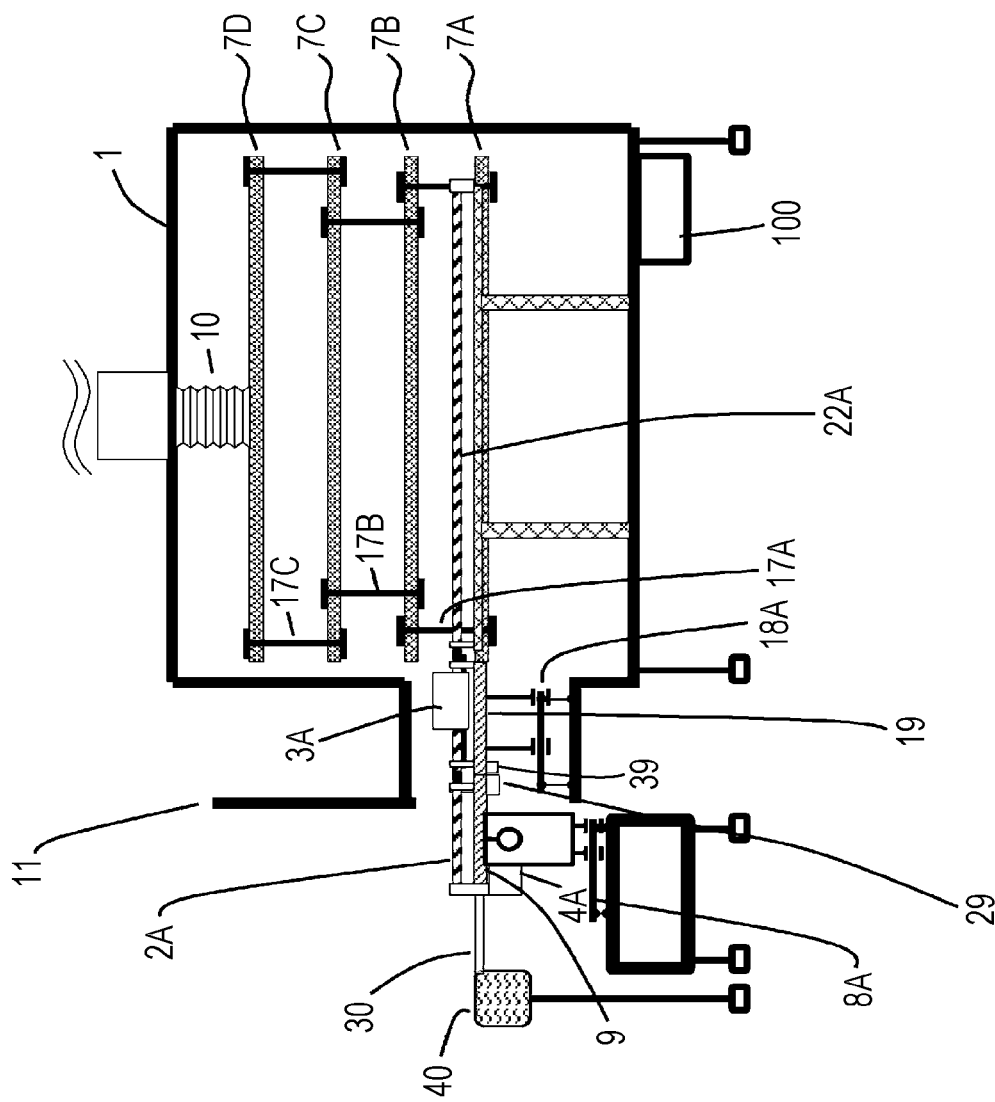
FIG. 11 is a schematic side view of the conveyance system according to the first embodiment.

As illustrated in FIG. 10, the first rod-like member 2A is a magnetic screw including a hard magnetic body, in which an S-pole magnetized band and an N-pole magnetized band are alternately provided in a spiral shape around the outer peripheral surface. The first rod-like member 2A may be inserted into a non-magnetic thin-wall pipe 20A. The pipe 20A is made of, for example, stainless steel. The first rod-like member 2A and the pipe 20A are formed into a single unit, so that when the first rod-like member 2A rotates, the pipe 20A also rotates around the central axis of the first rod-like member 2A. The first rod-like member 2B and the second and third rod-like members 12A, 12B, 22A, and 22B illustrated in FIG. 1 have the same structure as the structure of the first rod-like member 2A.

The moving member 3A includes a magnetic body and has a structure facing part of the peripheries of the first, second, and third rod-like members 2A, 12A, and 22A. For example, the moving member 3A includes a magnetic nut including a hard magnetic body and has a hole having an inner perimeter larger than the outer perimeter of the first rod-like member 2A. As illustrated in FIG. 10, the first rod-like member 2A passes through the hole of the nut-shaped moving member 3A. The inner circumferential surface of the hole of the moving member 3A is provided with an S-pole magnetized band and an N-pole magnetized band alternately in a spiral shape. The pitch of the magnetized band of the moving member 3A is substantially the same as the pitch of the magnetized band of the first rod-like member 2A. Guide rings 31 and 32, such as bushes, may be disposed on the inner circumferential surface of the moving member 3A. The inner circumference of each of the guide rings 31 and 32 is smaller than the inner circumference of the moving member 3A and is contact with the outer circumferential surface of the pipe 20A. This allows a constant space to be kept between the magnetized band of the first rod-like member 2A and the magnetized band of the moving member 3A. The guide rings 31 and 32 are made of a material having a small friction coefficient such as fluororesin. The moving member 3B illustrated in FIG. 1 has the same structure as that of the moving member 3A.

As illustrated in FIGS. 7, 8, 11, 12, and 13, when the drive unit 4A rotates the first rod-like member 2A, with the first, second, and third rod-like members 2A, 12A, and 22A connected to each other, the second and third rod-like members 12A and 22A also rotate. When the first, second, and third rod-like members 2A, 12A, and 22A rotate, a magnetic force acts between the magnetized bands of the first, second, and third rod-like members 2A, 12A, and 22A and the magnetized band of the moving member 3A to move the moving member 3A along the central axes of the first, second, and third rod-like members 2A, 12A, and 22A.

The drive unit 4B rotates the first rod-like member 2B in synchronization with the drive unit 4A. The moving member 3B moves along the central axes of the first, second, and third rod-like members 2B, 12B, and 22B in synchronization with the moving member 3A.

Figure 14:
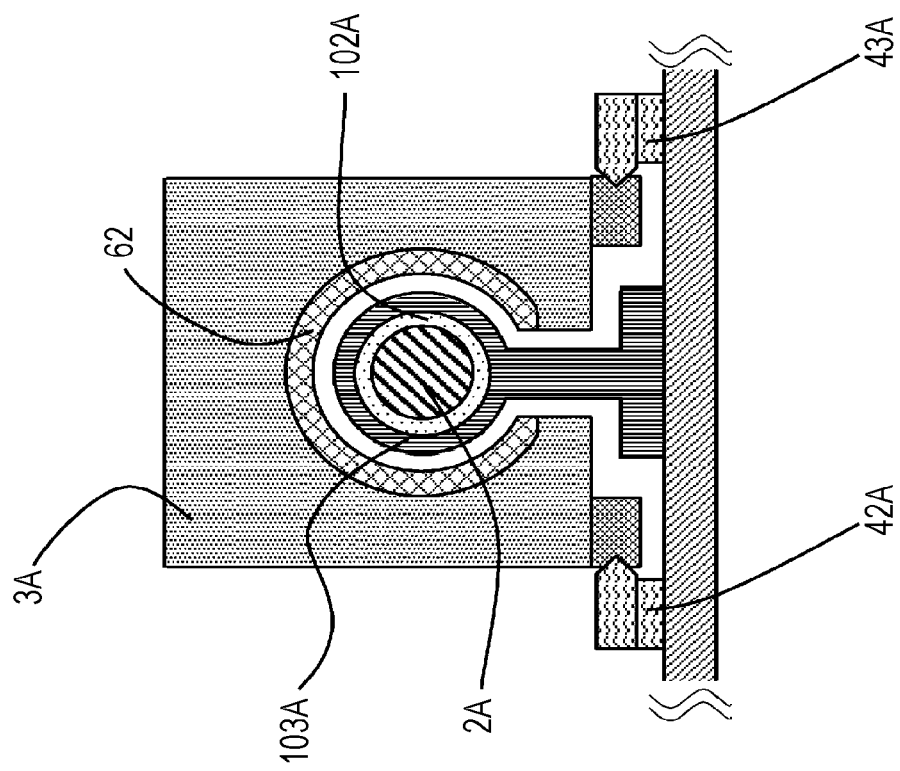
FIG. 14 is a schematic sectional view of the rod-like member, the moving member, and so on of the conveyance system according to the first embodiment.

The first, second, and third rod-like members 2A, 2B, 12A, 12B, 22A, and 22B are each held by, for example, a support and a bearing, disposed so as not to interfere with the movement of the moving members 3A and 3B. For example, as illustrated in FIG. 14, the first rod-like member 2A is held by a bearing 102 and a support 103A for the bearing 102A. The moving member 3A including a magnetic body 62 therein may be guided by guides 42A and 43A.

Figure 12:
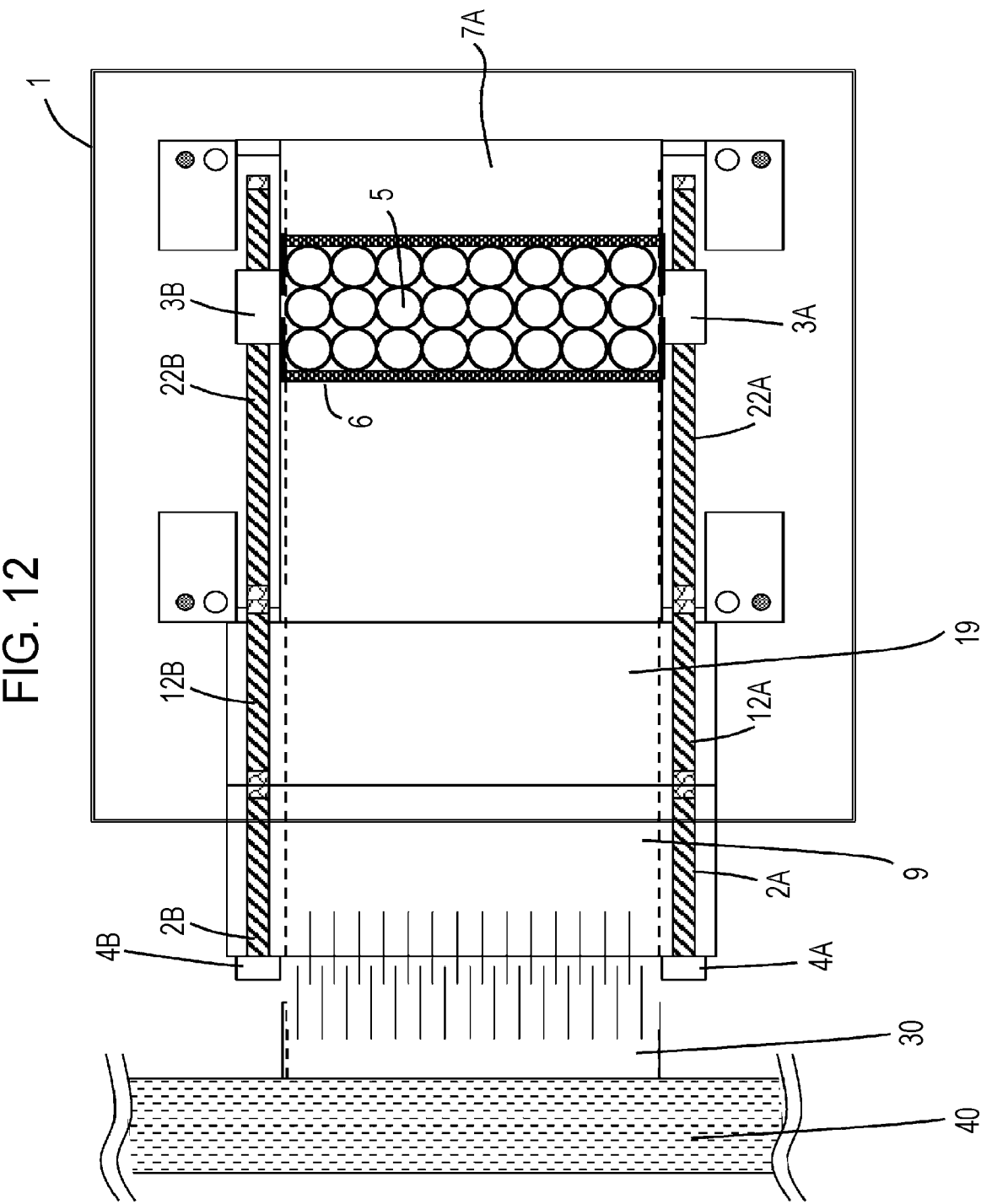
FIG. 12 is a schematic top view of the conveyance system according to the first embodiment.
Figure 13:
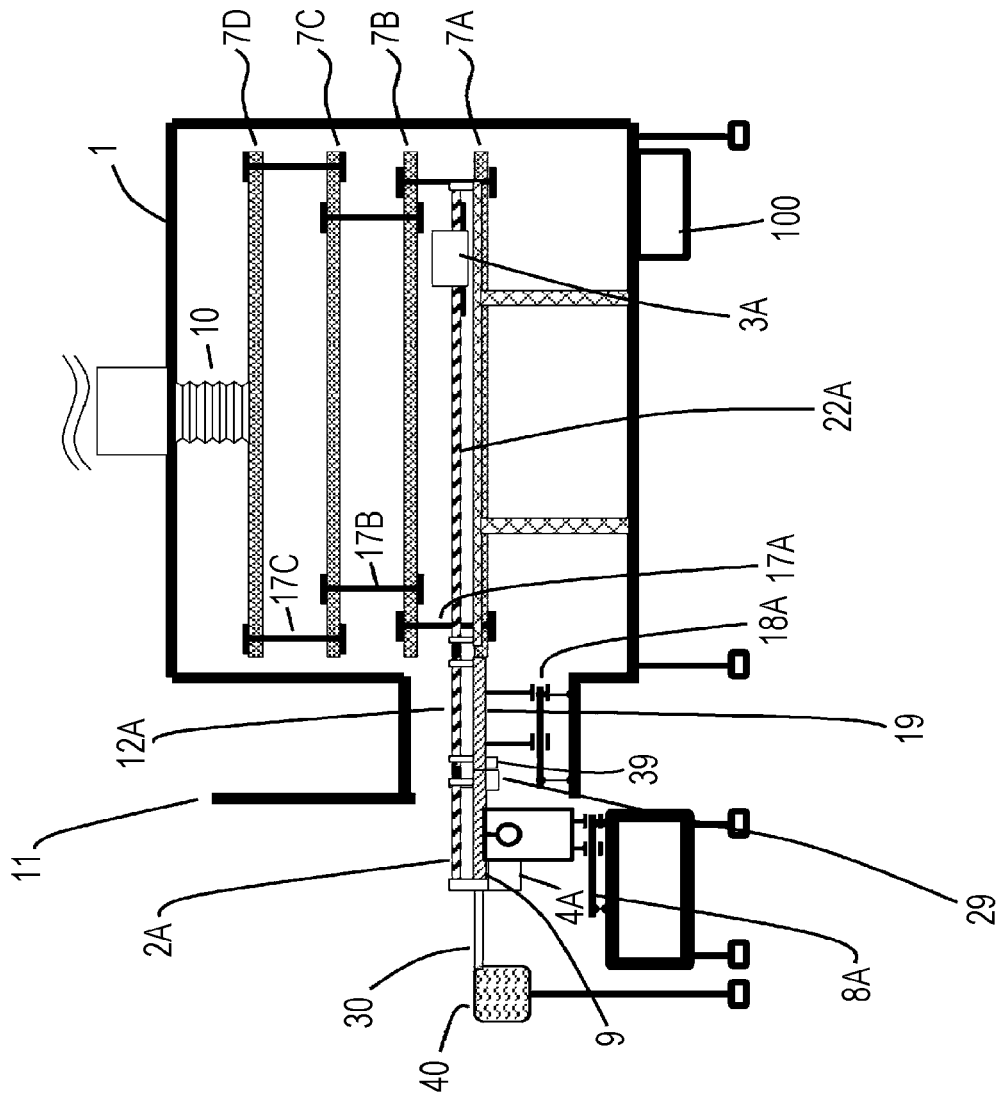
FIG. 13 is a schematic side view of the conveyance system according to the first embodiment.

As illustrated in FIGS. 1, 7, and 12, a contact member 6 that is in contact with the articles 5 and conveys the articles 5 inside and outside the chamber 1 is connected between the moving members 3A and 3B. The contact member 6 moves with the movement of the moving members 3A and 3B to move the articles 5 on the out-of-chamber bridge 9 onto the plate 7A in the chamber 1 via the in-chamber bridge 19. The contact member 6 also moves the articles 5 on the plate 7A in the chamber 1 onto the out-of-chamber bridge 9 via the in-chamber bridge 19.

Figure 15:
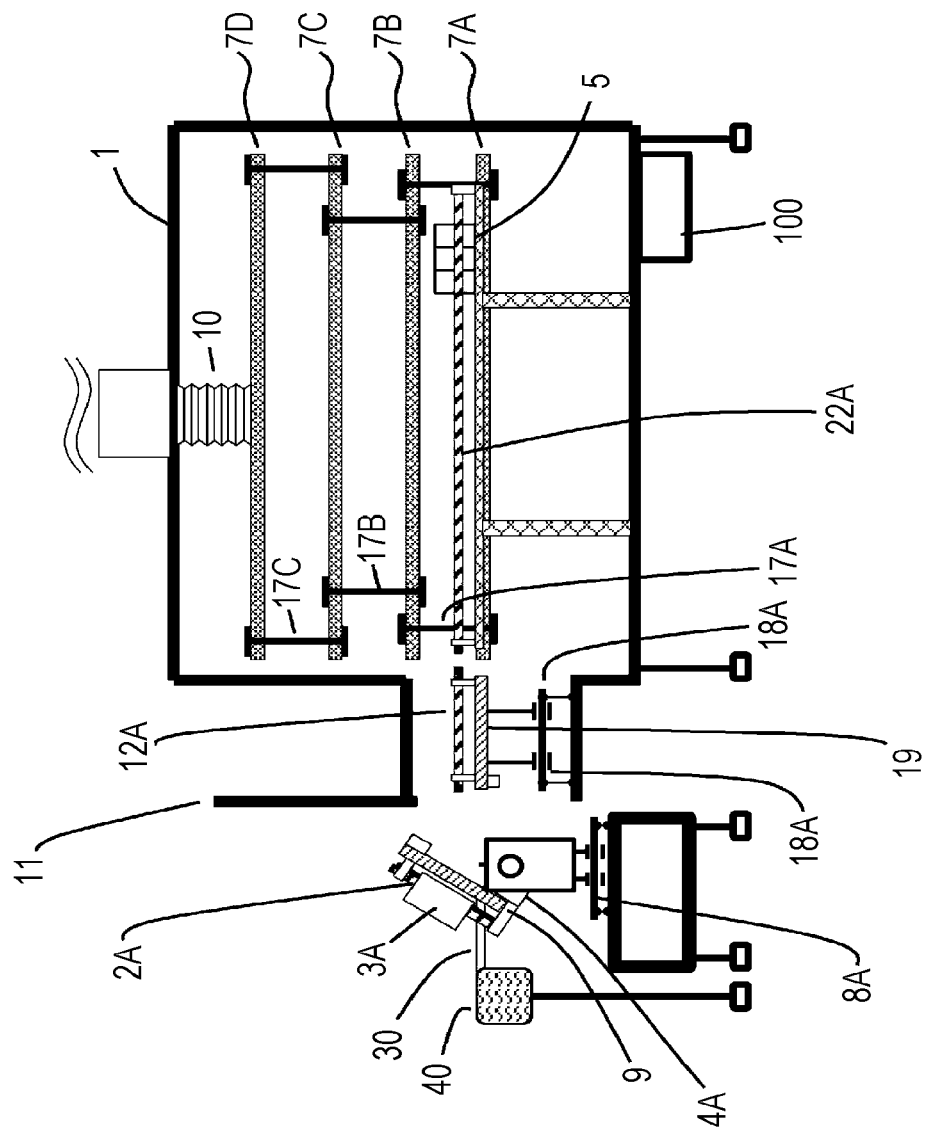
FIG. 15 is a schematic side view of the conveyance system according to the first embodiment.
Figure 16:
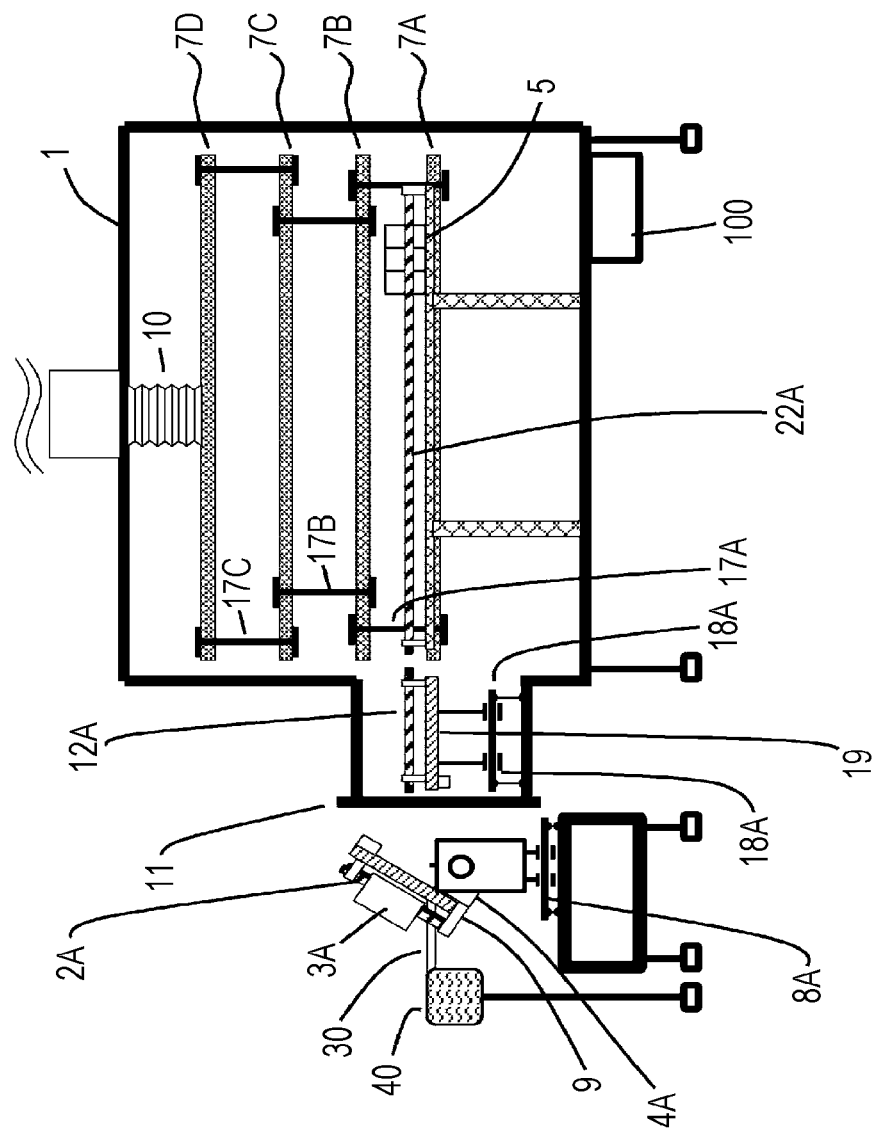
FIG. 16 is a schematic side view of the conveyance system according to the first embodiment.

For example, when substances in the articles 5 are to be freeze-dried, the moving member 3A moves onto the out-of-chamber bridge 9, with the articles 5 left on the plate 7A in the chamber 1, as illustrated in FIG. 15. At that time, if the moving member 3A outside the chamber 1 or the out-of-chamber bridge 9 interferes with the closing of the door 11 of the chamber 1, the out-of-chamber bridge 9 may rotate around a central axis parallel to the surface of the out-of-chamber bridge 9 and perpendicular to the moving direction of the moving member 3A. After the door 11 is closed, as illustrated in FIG. 16, the substances in the articles 5 are freeze-dried in the chamber 1.

Even if the out-of-chamber bridge 9 is rotated, the moving member 3A is held on the out-of-chamber bridge 9 due to the magnetic force between the first rod-like member 2A and the moving member 3A. Alternatively, the moving member 3A may be held on the out-of-chamber bridge 9 using another mechanism. The drive unit 4A that rotates the first rod-like member 2A may rotate together with the out-of-chamber bridge 9.

Figure 17:
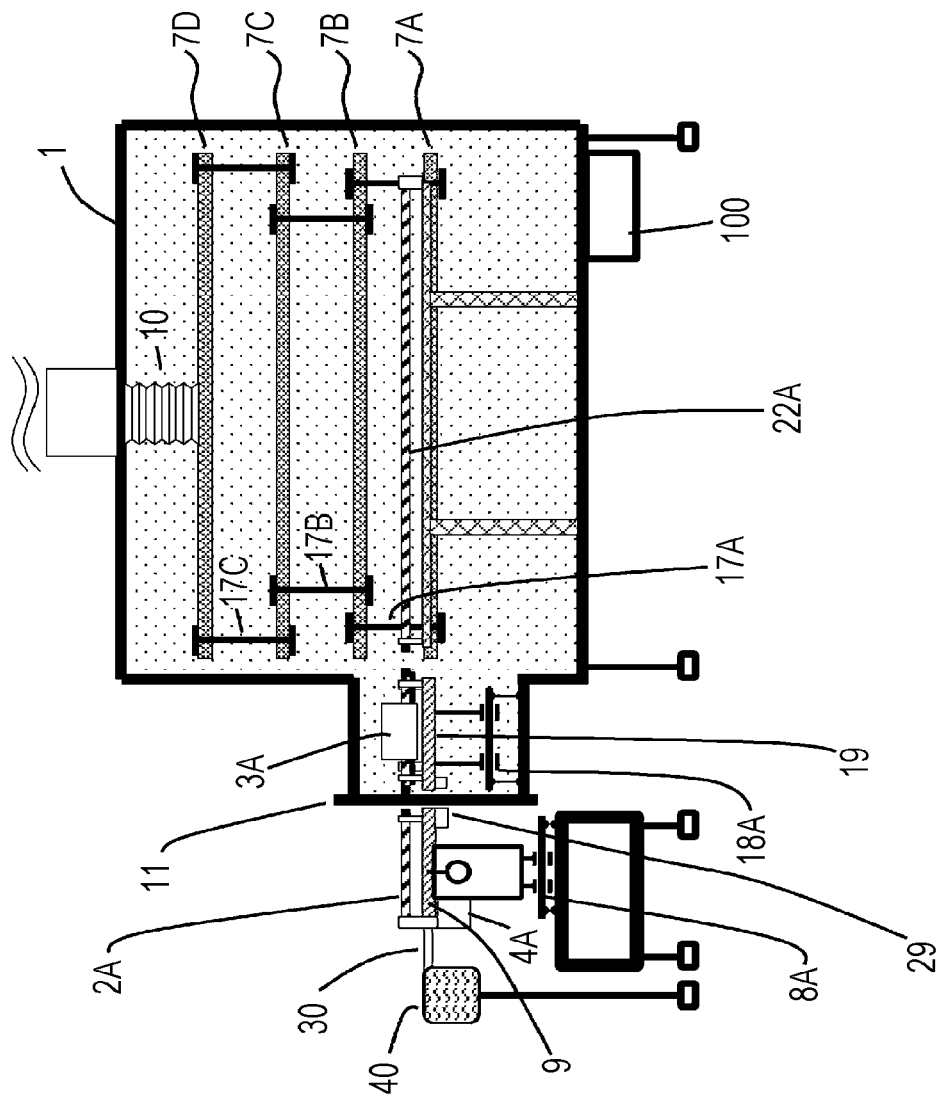
FIG. 17 is a schematic side view of the conveyance system according to the first embodiment.
Figure 18:
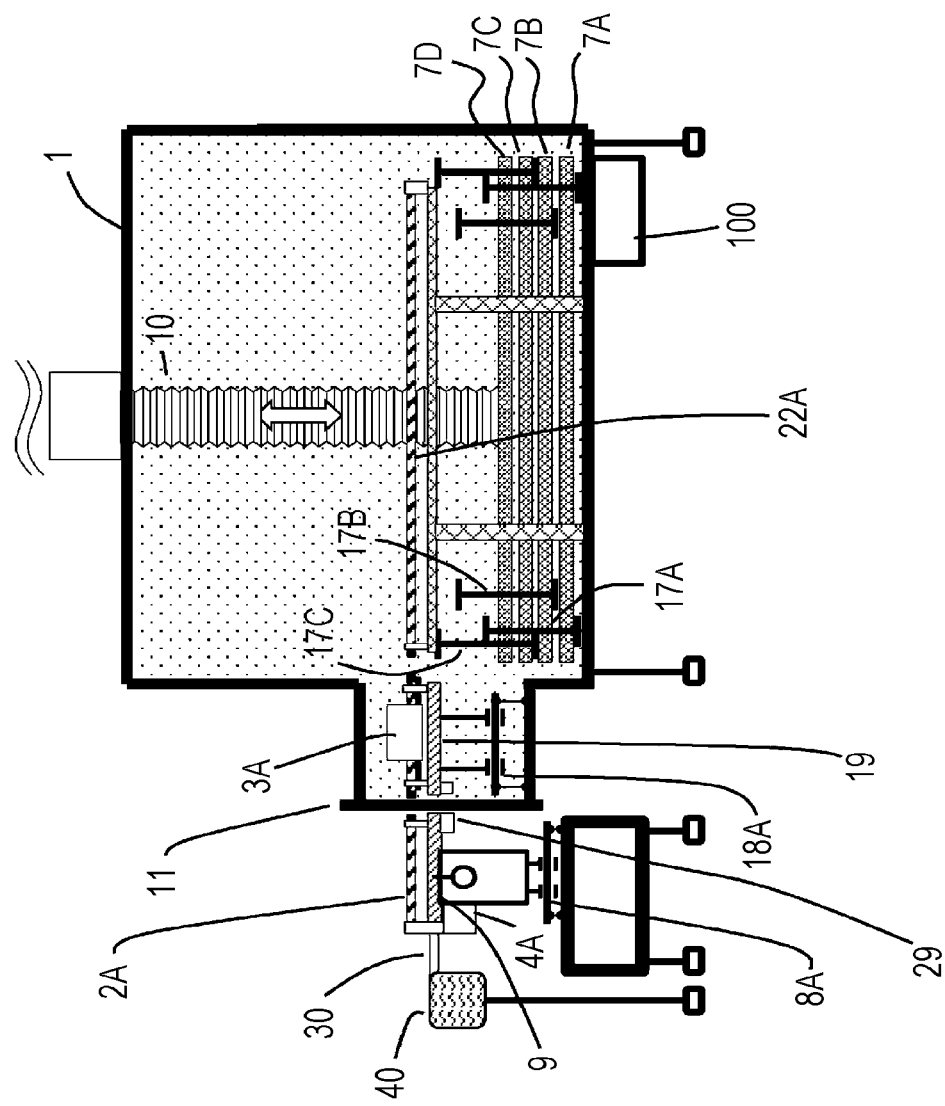
FIG. 18 is a schematic side view of the conveyance system according to the first embodiment.
Figure 19:
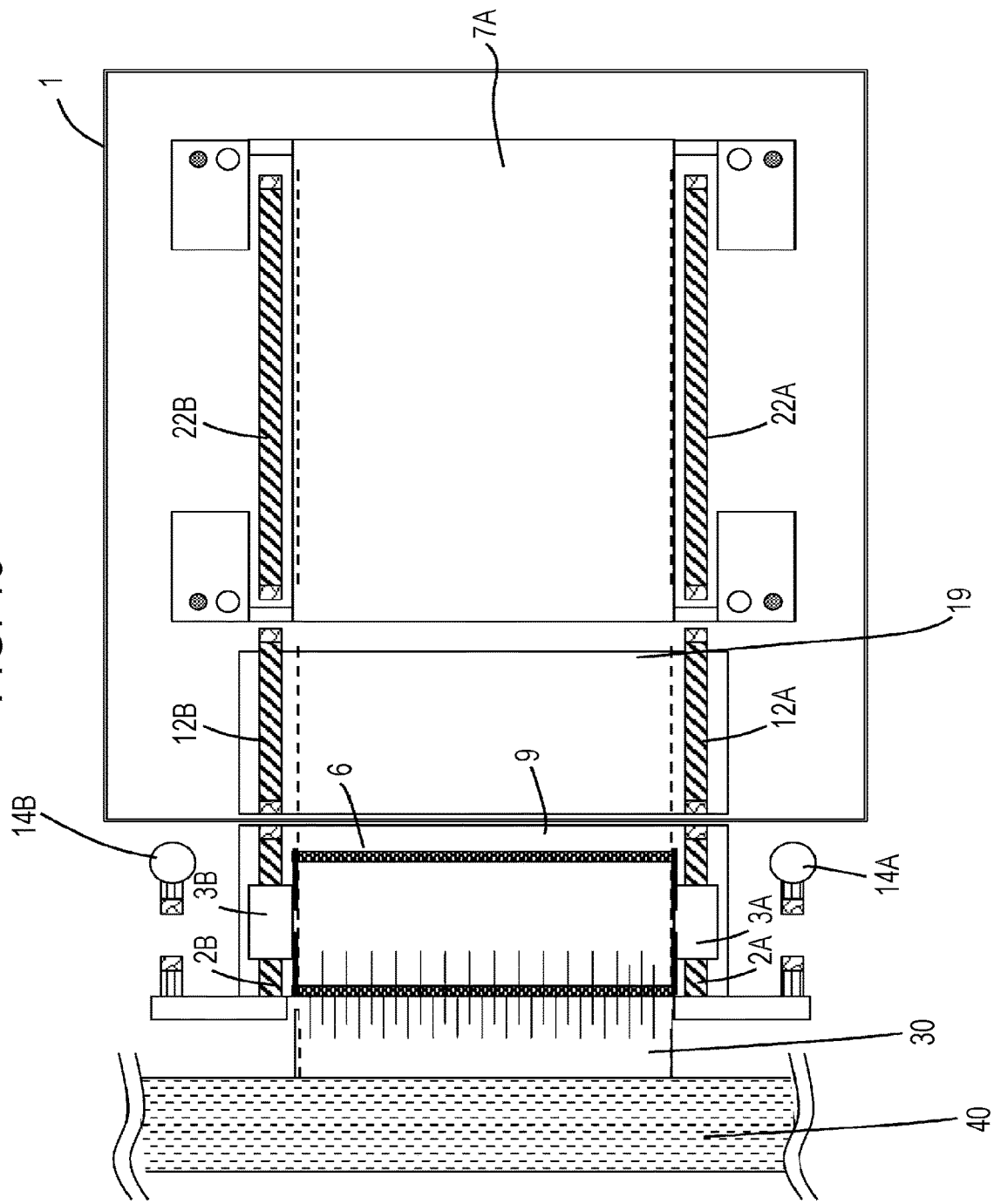
FIG. 19 is a schematic top view of a conveyance system of a modification of the first embodiment.

When the interior of the chamber 1 and the moving member 3A are to be sterilized, the moving member 3A is disposed on the in-chamber bridge 19, the out-of-chamber bridge 9 is separated from the in-chamber bridge 19, and the door 11 of the chamber 1 is closed to tightly seal the chamber 1, as illustrated in FIG. 17. Thereafter, the sterilization device 100 sterilizes the interior of the chamber 1 with high-pressure steam. At that time, the components in the chamber 1 can be thoroughly sterilized by moving the cylinder covered with the bellows cover 10 downward to extend the contracted bellows cover 10, as illustrated in FIG. 19, and by contracting the bellows cover 10. However, if the moving member 3A is present at a position along the plate 7A, the moving member 3A may interfere with the downward movement of the plate 7B, so that the bellows cover 10 cannot be sufficiently extended.

In contrast, in the conveyance system according to the first embodiment, the door 11 of the chamber 1 can be closed by disposing the moving member 3A on the in-chamber bridge 19 different from the plate 7A. This allows the bellows cover 10 to be sufficiently and fully extended and the moving member 3A to be sterilized.

Modification of First Embodiment

Figure 20:
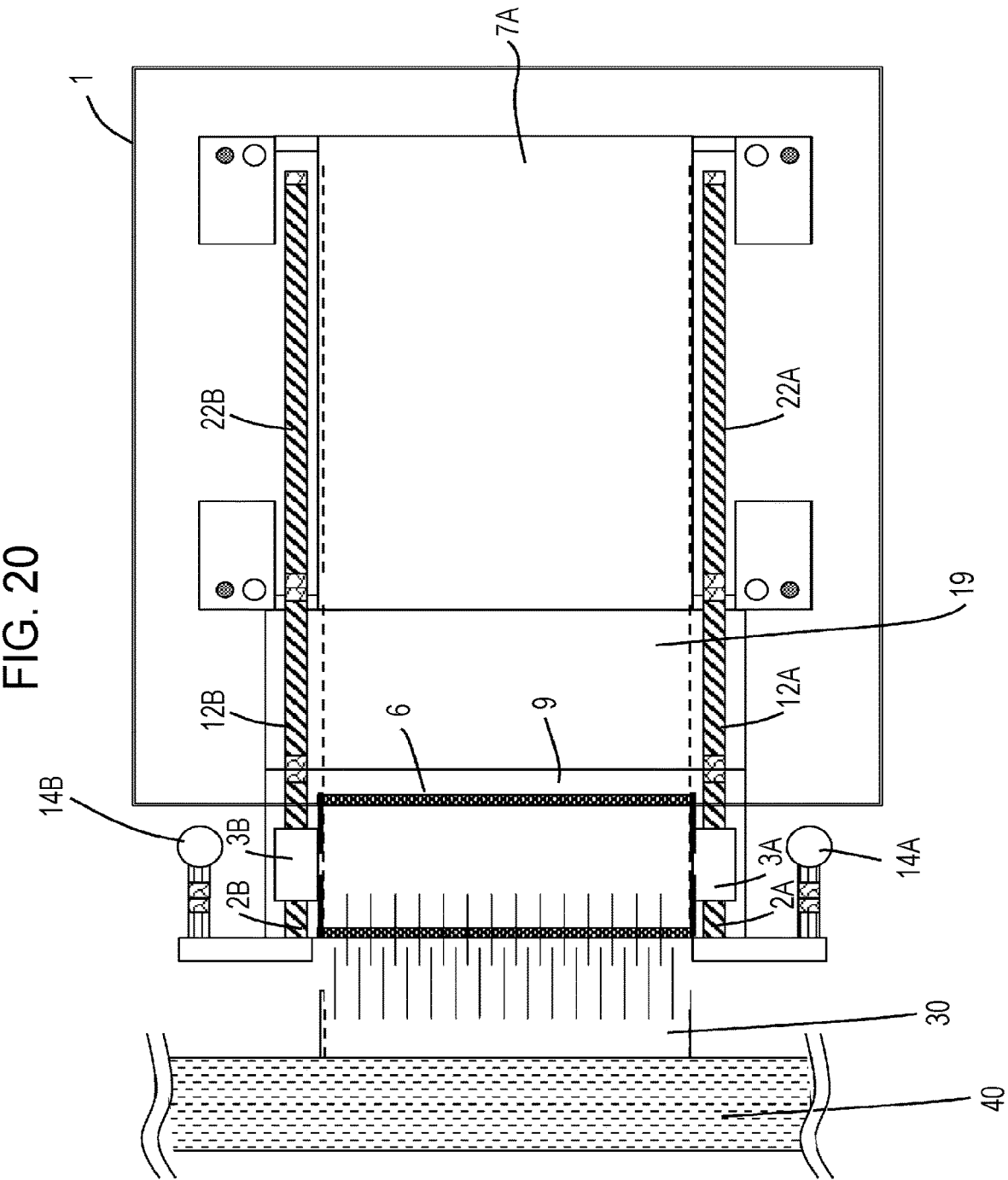
FIG. 20 is a schematic top view of the conveyance system of the modification of the first embodiment.

FIG. 16 illustrates an example in which the drive unit 4A rotates along with the out-of-chamber bridge 9. In contrast, as illustrated in FIGS. 19 and 20, when the out-of-chamber bridge 9 is inclined, drive units 14A and 14B that rotate the first rod-like members 2A and 2B may be separated from the first rod-like members 2A and 2B, and when the surface of the out-of-chamber bridge 9 is parallel to the surface of the in-chamber bridge 19, the drive units 14A and 14B may be connected to the first rod-like members 2A and 2B by a coupler or a driving transmission mechanism.

Second Embodiment

Figure 21:
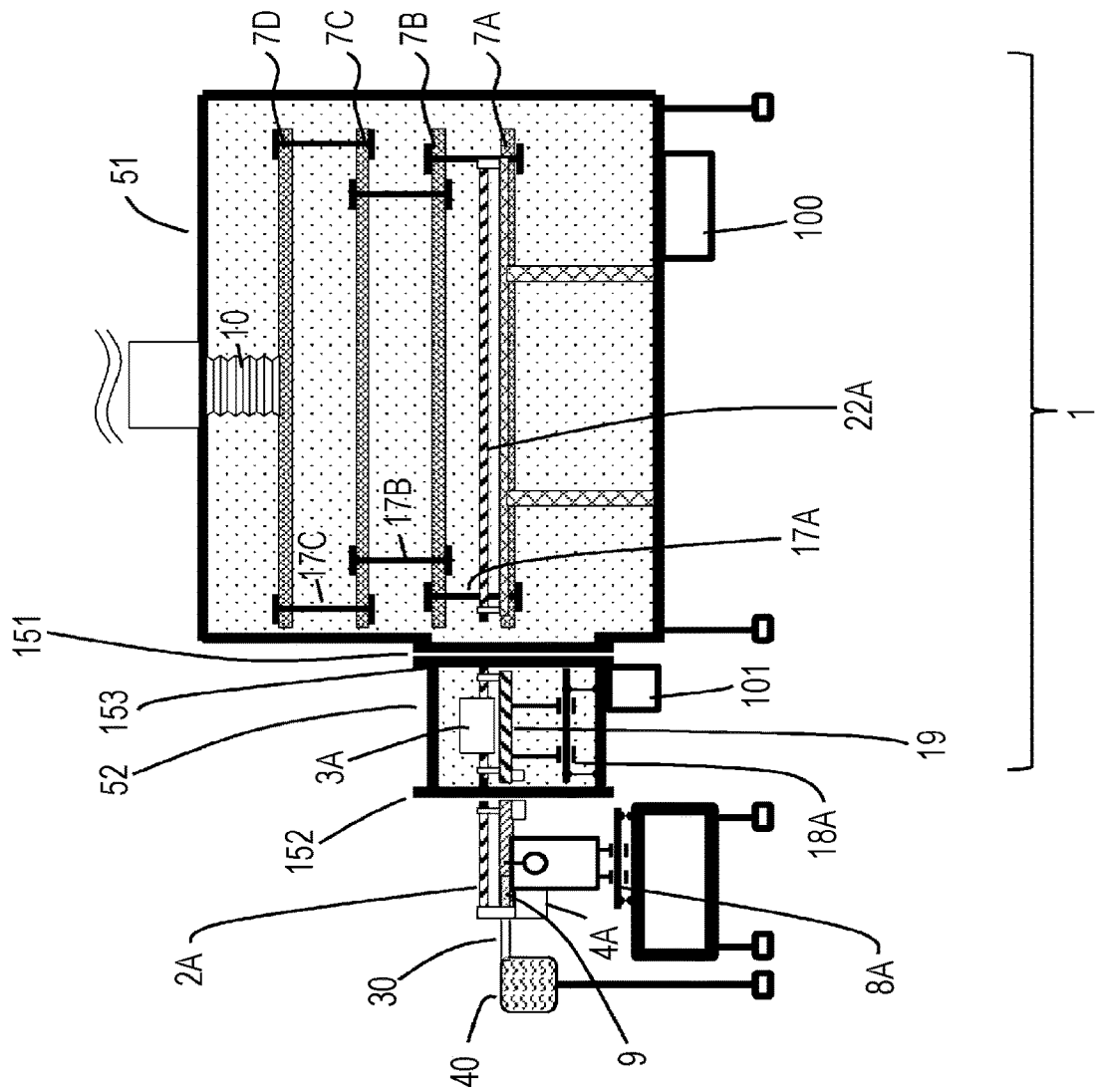
FIG. 21 is a schematic side view of a conveyance system according to a second embodiment.

In a conveyance system according to a second embodiment, as illustrated in FIG. 21, the chamber 1 includes a first chamber 51 containing the plate 7A and having a first door 151 between the in-chamber bridge 19 and the plate 7A and a second chamber 52 containing the in-chamber bridge 19 and having a second door 152 between the out-of-chamber bridge 9 and the in-chamber bridge 19 and a third door 153 between the in-chamber bridge 19 and the plate 7A.

The first door 151 of the first chamber 51 and the second and third doors 152 and 153 of the second chamber 52 can be closed, with the moving member 3A disposed on the in-chamber bridge 19. This allows each of the first chamber 51 and the second chamber 52 to be tightly sealed. The conveyance system according to the second embodiment further includes the sterilization device 100 that sterilizes the interior of the first chamber 51 and a sterilization device 101 that sterilizes the interior of the second chamber 52.

The other components of the conveyance system according to the second embodiment are similar to those of the first embodiment. The conveyance system according to the second embodiment can sterilize, for example, the interior of the first chamber 51 and the interior of the second chamber 52 on different conditions.

Other Embodiments

Having described the present invention as related to the embodiments, it should not be understood that the description and drawings constituting part of the present disclosure limit the present invention. It is obvious to those skilled in the art that various alternative embodiments, examples, and operational techniques can be made from the present disclosure.

Figure 22:
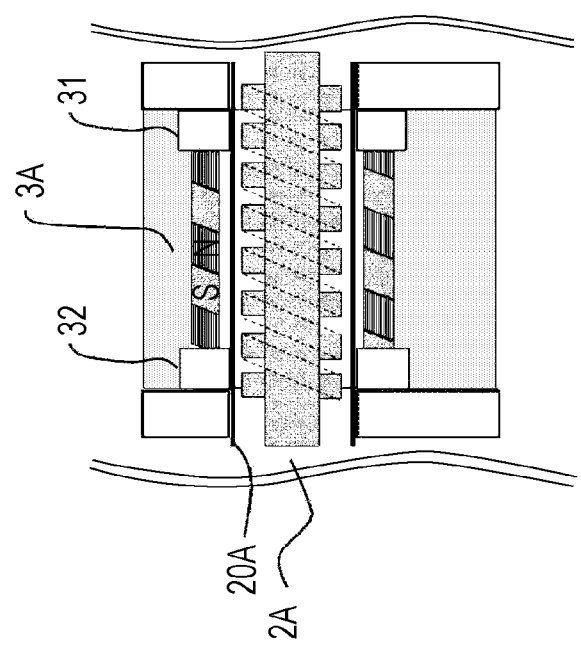
FIG. 22 is a schematic side view of a rod-like member and a moving member according to another embodiment.

For example, the configurations of the rod-like member 2A and the moving member 3A are not limited to the example illustrated in FIG. 10. For example, as illustrated in FIG. 22, the first rod-like member 2A may be a soft threaded magnetic body. The configuration of the moving member 3A is the same as that in FIG. 10. The pitch of the screw thread of the first rod-like member 2A illustrated in FIG. 22 is substantially the same as the pitch of the magnetized band of the moving member 3A. The threaded first rod-like member 2A may be inserted into the non-magnetic thin-wall pipe 20A. This makes it possible to prevent foreign matter from adhering to the thread groove of the rod-like member 2A. When the first rod-like member 2A is rotated, a magnetic force acts between the screw thread of the first rod-like member 2A and the magnetized band of the moving member 3A to move the moving member 3A.

Figure 23:
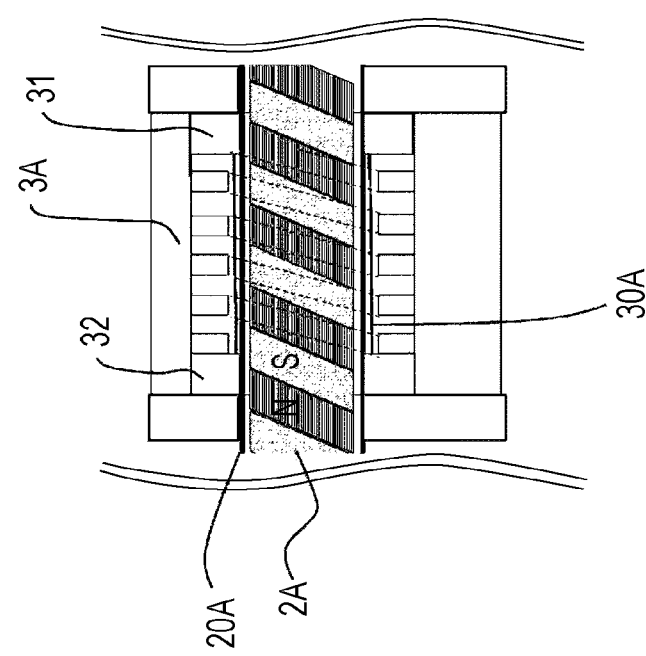
FIG. 23 is a schematic side view of a rod-like member and a moving member according to a yet another embodiment.

Alternatively, as illustrated in FIG. 23, the moving member 3A may be a threaded soft magnetic body. The surface of the threaded hole of the moving member 3A may be covered with a non-magnetic thin-wall pipe 30A. This makes it possible to prevent foreign matter from adhering to the thread groove of the moving member 3A. The configuration of the rod-like member 2A is the same as that in FIG. 10. The pitch of the screw thread of the moving member 3A illustrated in FIG. 23 is substantially the same as the pitch of the magnetized band of the first rod-like member 2A. When the first rod-like member 2A is rotated, a magnetic force acts between the magnetized band of the first rod-like member 2A and the screw thread of the moving member 3A to move the moving member 3A.

For example, the content of the articles conveyed inside and outside the chamber is not only a pharmaceutical but also includes food, drink, precision components, and any other objects. The chamber is not limited to the freeze-drying chamber but may be a fermentation chamber or all kinds of chambers where suppression of unevenness in the temperature distribution inside and suppression of dust generation are desired. The shape of the moving member is not limited to the nut shape but may be, for example, a recessed shape. In this case, the rod-like member passes through the recessed portion of the recessed moving member. An S-pole magnetized band and an N-pole magnetized band are alternately provided on the periphery of the recessed portion of the recessed moving member.

Figure 24:
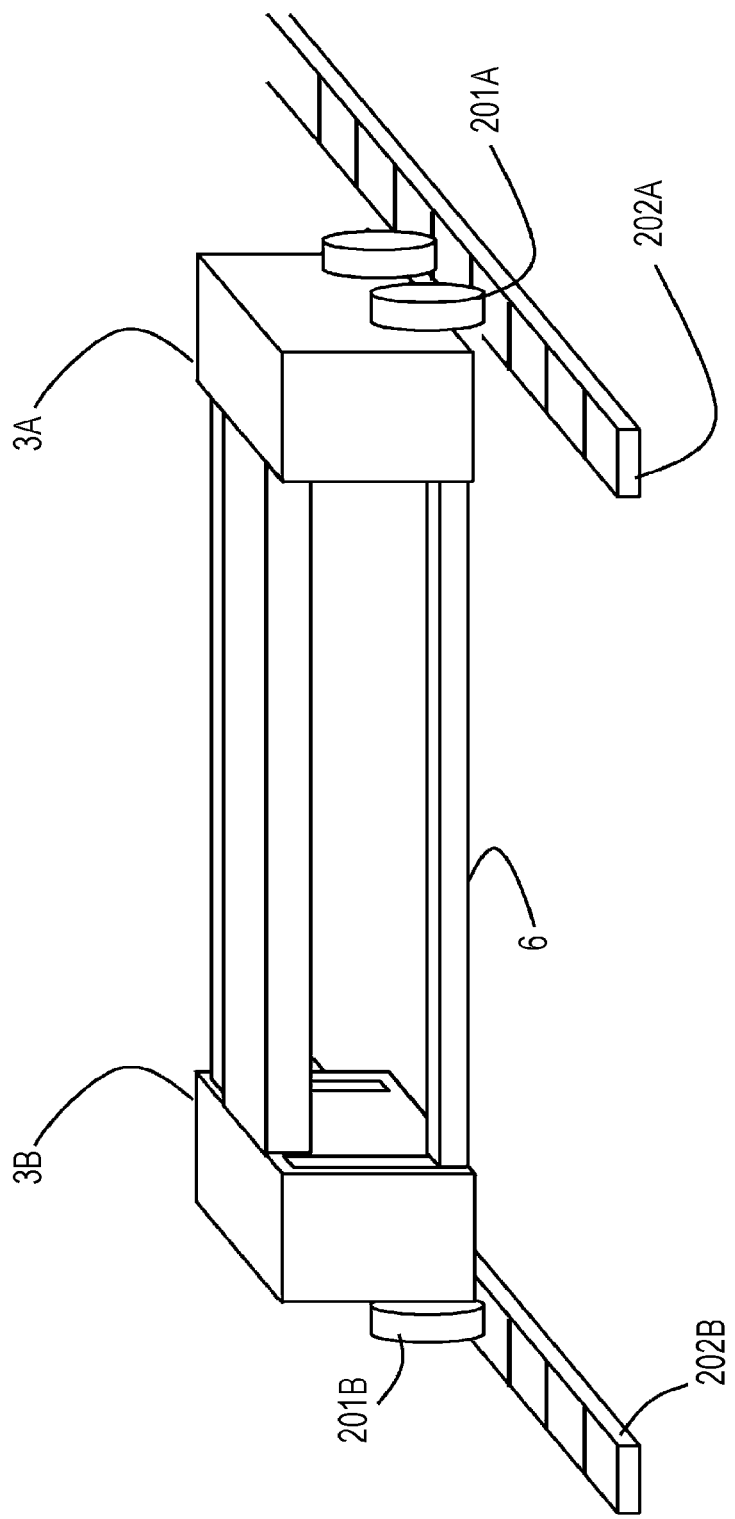
FIG. 24 is a schematic perspective view of a moving member according to a yet further embodiment.

The moving members 3A and 3B are not necessarily be driven using the magnetic screw. For example, as illustrated in FIGS. 24 and 25, the moving member 3A may include wheels 201A that rotate on a railroad 202A and a drive unit 203A for rotating the wheels 201A so as to be self-propelled. The shafts of the wheels 201A may be held by bearings 207A. The drive unit 203A may be controlled by a control unit 204A. The details of control of the control unit 204A may be remotely indicated from the outside via a receiver 205A. The moving member 3A may include a battery 206A for supplying power to the drive unit 203A and so on.

Thus, it is to be understood that the present invention includes various embodiments not described here.

REFERENCE SIGNS LIST 1 chamber
2A, 2B, 12A, 12B, 22A, 22B rod-like member
3A, 3B moving member
4A, 4B, 14A, 14B drive unit
5 article
6 contact member
7A, 7B, 7C, 7D plate
8A, 18A guide rail
9 out-of-chamber bridge
10 bellows cover
11, 151, 152, 153 door
17A, 17B, 17C hook
19 in-chamber bridge
20A, 30A pipe
29, 39 coupler
30 fixing plate 31 guide ring
40 conveyer
51 first chamber
52 second chamber
100, 101 sterilization device

The invention claimed is:

1. A conveyance system comprising:
   a chamber;
   a plate disposed in the chamber, the plate being used for disposing an article thereon;
   an in-chamber bridge disposed next to the plate in the chamber;
   a moving member that moves along the in-chamber bridge and the plate to move the article on the in-chamber bridge and the plate; and
   a sterilization device that sterilizes an interior of the chamber,
   wherein the chamber is allowed to be tightly sealed, with the moving member disposed on the in-chamber bridge.

2. The conveyance system according to claim 1, wherein the sterilization device pressurizes the interior of the chamber.

3. The conveyance system according to claim 1, wherein the sterilization device heats the interior of the chamber.

4. The conveyance system according to claim 1, further comprising:
   an out-of-chamber bridge disposed outside a door of the chamber, the out-of-chamber bridge being contactable with the in-chamber bridge,
   wherein the moving member moves along the out-of-chamber bridge, the in-chamber bridge, and the plate.

5. The conveyance system according to claim 4, wherein the in-chamber bridge is movable between the out-of-chamber bridge and the plate.

6. The conveyance system according to claim 4, wherein the out-of-chamber bridge is movable toward the in-chamber bridge.

7. The conveyance system according to claim 4, wherein the out-of-chamber bridge is rotatable.

8. The conveyance system according to claim 4, further comprising:
   a first rod-like member disposed at the out-of-chamber bridge and including a magnetic body;
   a second rod-like member disposed at the in-chamber bridge and including a magnetic body;
   a third rod-like member disposed along the plate in the chamber and including a magnetic body; and
   a drive unit that rotates the first rod-like member,
   wherein, when the out-of-chamber bridge, the in-chamber bridge, and the plate come into contact with each other, the first, second, and third rod-like members are connected to each other,
   wherein the moving member includes a magnetic body and faces part of peripheries of the first to third rod-like members, and
   wherein the moving member moves along the first, second, and third rod-like members as the first, second, and third rod-like members rotate.

9. The conveyance system according to claim 4,
   wherein the chamber includes
   a first chamber containing the plate and including a first door between the in-chamber bridge and the plate; and
   a second chamber containing the in-chamber bridge and including a second door between the out-of-chamber bridge and the in-chamber bridge, and
   wherein the first and second doors are allowed to be closed, with the moving member disposed on the in-chamber bridge.

10. The conveyance system according to claim 1, further comprising a contact member connected to the moving member and being in contact with the article.

* * * * *